(12) United States Patent
Dubovoy et al.

(10) Patent No.: US 11,690,833 B2
(45) Date of Patent: Jul. 4, 2023

(54) PERSONAL CARE COMPOSITIONS

(71) Applicant: Colgate-Palmolive Company, New York, NY (US)

(72) Inventors: Viktor Dubovoy, Cresskill, NJ (US); Junhong Mao, Plainsboro, NJ (US); Ravi Subramanyam, Belle Mead, NJ (US); Long Pan, Somerset, NJ (US); Tatiana Brinzari, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 287 days.

(21) Appl. No.: 16/955,160

(22) PCT Filed: Dec. 7, 2018

(86) PCT No.: PCT/US2018/064562
§ 371 (c)(1),
(2) Date: Jun. 18, 2020

(87) PCT Pub. No.: WO2019/125792
PCT Pub. Date: Jun. 27, 2019

(65) Prior Publication Data
US 2020/0316044 A1    Oct. 8, 2020

Related U.S. Application Data

(60) Provisional application No. 62/607,355, filed on Dec. 19, 2017.

(51) Int. Cl.
*A61K 31/4425* (2006.01)
*A61K 47/52* (2017.01)

(52) U.S. Cl.
CPC .......... *A61K 31/4425* (2013.01); *A61K 47/52* (2017.08)

(58) Field of Classification Search
CPC ........................... A61K 31/4425; A61K 47/52
See application file for complete search history.

(56) References Cited

U.S. PATENT DOCUMENTS

| | | | |
|---|---|---|---|
| 4,146,607 A | 3/1979 | Ritchey | |
| 4,578,489 A * | 3/1986 | Wehner | A01N 55/04 504/191 |
| 5,300,289 A | 4/1994 | Garlich et al. | |
| 5,948,390 A | 9/1999 | Nelson et al. | |
| 9,504,858 B2 | 11/2016 | Yuan | |
| 9,861,563 B2 | 1/2018 | Kirkpatrick-Liverman et al. | |
| 10,703,766 B2 * | 7/2020 | Dubovoy | A61K 8/4926 |
| 11,384,101 B2 * | 7/2022 | Dubovoy | A61K 8/4926 |
| 2010/0015245 A1 * | 1/2010 | Harrison | A01N 59/16 424/615 |
| 2012/0034280 A1 * | 2/2012 | Cohen | A61K 45/06 424/53 |
| 2012/0177747 A1 * | 7/2012 | Sookram | A01N 43/40 424/641 |
| 2019/0185490 A1 * | 6/2019 | Dubovoy | A61K 8/19 |
| 2020/0291047 A1 * | 9/2020 | Dubovoy | C07F 7/2208 |
| 2021/0275581 A1 * | 9/2021 | Dubovoy | A61Q 11/00 |

FOREIGN PATENT DOCUMENTS

| | | |
|---|---|---|
| DE | 102011088944 | 6/2013 |
| EP | 3187576 | 7/2017 |
| JP | H08-053313 | 2/1996 |
| JP | 2009292739 A * | 12/2009 |
| RO | 127465 A2 * | 6/2012 |
| RU | 2497496 | 11/2013 |
| RU | 2634261 | 10/2017 |
| RU | 2634269 | 10/2017 |
| WO | 2014/098827 | 6/2014 |
| WO | 2014/099164 | 6/2014 |

OTHER PUBLICATIONS

Bacitracin Zinc and Polymyxin B Sulfate Ophthalmic Ointment USP, Sterile. Package Insert. Sep. 2010. (Year: 2010).*
Dubovoy; ACS Omega 2020, 5, 18, 10359-10365. https://doi.org/10.1021/acsomega.0c00131 (Year: 2020).*
Neve; Inorganica Chimica Acta 2002, 338, 51-58. https://doi.org/10.1016/S0020-1693(02)00976-3 (Year: 2002).*
Kaur; Phys. Chem. Chem. Phys.,2016, 18, 23961. https://doi.org/10.1039/C6CP03070J (Year: 2016).*
Machine English Translation of RO-127465-A2 from Espacenet (Year: 2012).*
Kang; Archives of Oral Biology 2017, 84, 133-138. http://dx.doi.org/10.1016/j.archoralbio.2017.09.023 (Year: 2017).*
Giertsen; Scandinavian Journal of Dental Research 1991, 99, 301-309. DOI: 10.1111/j.1600-0722.1991.tb01032.x. CAS Scifinder Abstract. (Year: 1991).*
International Search Report and Written Opinion of the International Searching Authority in International Application No. PCT/US2018/064562, dated Mar. 19, 2019.
Mikurube et al., 2016, "Isomerization-induced introduction of metal cations into polyoxomolybdate-surfactant hybrid crystals", Inorganic Chemistry Communications. 73:45-48.
Palermo et al., 2016, "First Report About the Use of Micellar Keggin Heteropolyacids as Catalysts in the Green Multicomponent Synthesis of Nifedipine Derivatives", Catalysis Letters, 146(9):1634-1647.
Spurny et al., 1987, "Monatshefte tfir Chemie Chemical Monthly F~illung der anionischen Nitratkomplexe von Ce 4+ und Pu 4+ mit Cetylpyridiniumnitrat," Dezember 118:789-791.
Vo et al., 2012, "Noncovalent supramolecular assembly of hexagonally ordered mesoscale Prussian blue analogue," Microporous and Mesoporous Materials, 163:211-214.

(Continued)

*Primary Examiner* — Daniel R Carcanague

(57) ABSTRACT

Described herein are complexes comprising a cationic antibacterial agent and a metal salt, personal care compositions comprising same; along with methods of making and using these complexes and compositions.

7 Claims, 15 Drawing Sheets

(56) References Cited

OTHER PUBLICATIONS

Yu et al., 2014, "Oxidative Desulfurization of Diesel Using Organic Salt of Polyoxometalate as an Efficient and Recoverable Phase-transfer Catalyst," Chemistry Letters, 43(6):834-836.
He, Handbook of Water Treatment Chemicals, Chemical Industry Press, p. 296, May 31, 2000.
Li et al., Instant Reference Manual of Surgical Drugs, Hebei Science & Technology Press, p. 784, Jan. 31, 2004.

* cited by examiner

PERSONAL CARE COMPOSITIONS

CROSS-REFERENCE TO RELATED APPLICATIONS

This application claims priority to U.S. Provisional Patent Application Ser. No. 62/607,355, filed on Dec. 19, 2017, which is incorporated by reference herein in its entirety.

BACKGROUND

Antibacterial agents are commonly incorporated into a wide variety of personal care compositions, such as bar soaps, body washes, shampoos, and underarm products, to destroy or retard the growth of bacteria on the skin or hair and to combat malodor.

Many antibacterial agents are cationic in order to interact with the negatively-charged microbial cell membranes. However, since most bar soap is inherently strongly alkaline, antibacterial agents containing acidic or cationic functional groups may be deactivated when incorporated into bar soap compositions. Similarly, personal care formulations often include anionic soaps or surfactants, which can also deactivate cationic antibacterial agents.

Accordingly, it would be commercially desirable to have personal care compositions wherein highly efficacious cationic antibacterial agents can be formulated with anionic surfactant systems without a meaningful loss in antibacterial efficacy. Implementations of the present invention are designed to meet this, and other, needs.

BRIEF SUMMARY

This summary is intended merely to introduce a simplified summary of some aspects of one or more implementations of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a complex including a cationic antibacterial agent and a metal salt.

The metal salt may be a soluble metal salt.
The metal salt may be a divalent metal.
The metal salt may be selected from a zinc salt and a stannous salt.

The cationic antibacterial agent may be cetylpyridinium chloride (CPC) and the complex is a cetylpyridinium complex.

The molar ratio of the metal salt to cationic antibacterial agent may be from about 0.5:1 to about 2:1.

The metal salt may be a zinc salt and the cationic antibacterial agent is CPC.

The zinc salt may be selected from: zinc chloride, zinc sulfate, zinc nitrate, zinc bromide, and zinc citrate.

The complex may have a structural formula of $[(C_{21}H_{38}N)_2][ZnCl_4]$.

The metal salt may be a stannous salt and the cationic antibacterial agent may be CPC.

The complex may have a structural formula of $[C_2H_{38}N][SnCl_3]$.

The foregoing and/or other aspects and utilities embodied in the present disclosure may also be achieved by providing a personal care composition, including a complex including a cationic antibacterial agent and a metal salt; a surfactant; and a cosmetically acceptable carrier.

The metal salt may be a soluble metal salt.
The metal salt may be a divalent metal.
The soluble metal salt may be selected from a zinc salt and a stannous salt.

The zinc salt may be selected from: zinc chloride, zinc sulfate, zinc nitrate, zinc bromide, and zinc citrate.

The cationic antibacterial agent may be cetylpyridinium chloride (CPC).

The molar ratio of the metal salt to cationic antibacterial agent may be from about 0.5:1 to about 2:1.

The metal salt may be a zinc salt and the cationic antibacterial agent may be CPC and wherein the zinc salt may be zinc chloride.

The complex may have a structural formula of $[(C_{21}H_{38}N)_2][ZnCl_4]$.

The metal salt may be a stannous salt and the cationic antibacterial agent may be CPC.

The complex may have a structural formula of $[C_{21}H_{38}N][SnCl_3]$.

The surfactant may be an anionic surfactant selected from: sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylate, sodium dodecyl benzenesulfonate; and combinations of two or more thereof.

The personal care composition may include from about 0.01 weight % to about 8.0 weight % of said complex.

The personal care composition may include from about 0.10 weight % to about 0.75 weight % of said complex.

The personal care composition may be in a form selected from: a bar soap, a liquid hand soap, a shower gel, a body wash, a shampoo, a facial cleanser, a body wash, a cream, an antiperspirant, and a deodorant.

The personal care composition may be in the form of a bar soap.

The personal care composition may be in a form selected from an antiperspirant and a deodorant.

The personal care composition may further include one or more ingredients selected from a fragrance; a skin conditioning agent, a moisturizing agent, a dye, a pigment, a chelating agent, a sunscreen active ingredient, an antiaging compound, an antioxidant, a vitamin, an essential oil, and a combination of two or more thereof.

The foregoing and/or other aspects and utilities embodied in the present disclosure may also be achieved by providing a method of treating, inhibiting or preventing bacterial growth on a subject in need thereof, including applying a personal care composition as described above to the skin of said subject.

The foregoing and/or other aspects and utilities embodied in the present disclosure may also be achieved by providing the use of a personal care composition as described above to treat, prevent, or inhibit bacterial growth on a subject in need thereof.

Figure 1:
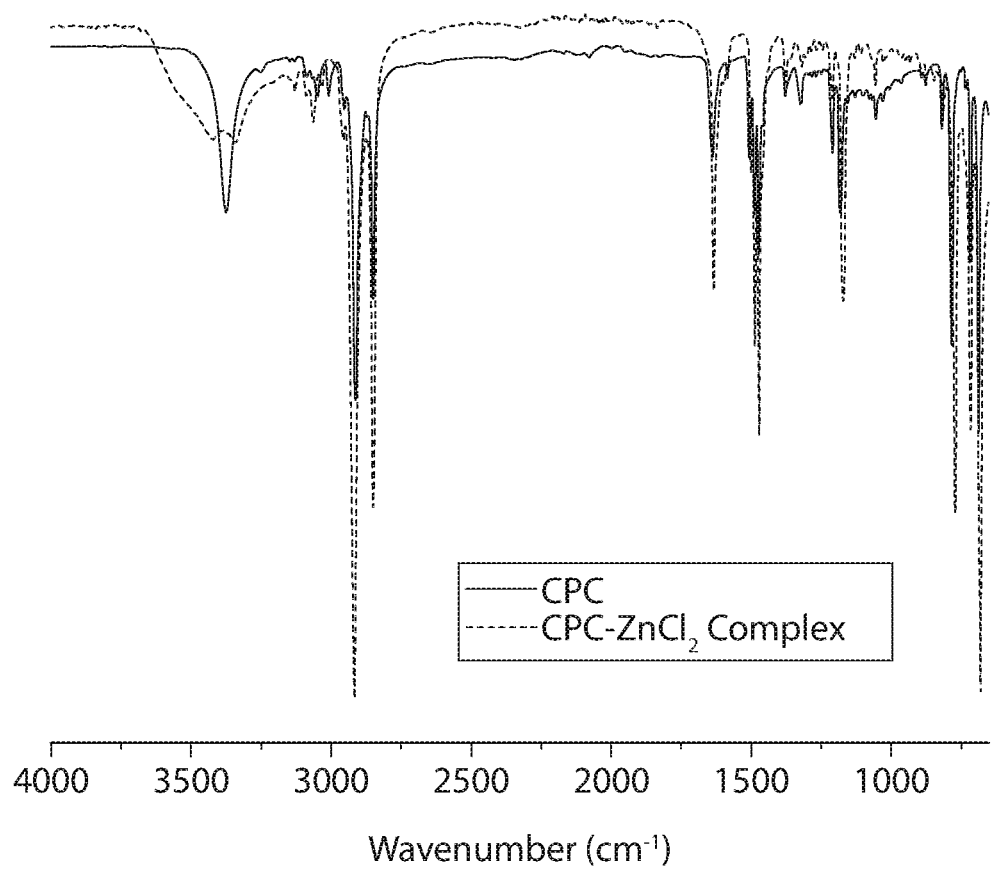
FIG. 1 illustrates the full spectrum (FTIR-ATR) infrared spectroscopy of samples of CPC—$ZnCl_2$ complex and CPC according to an implementation.

These drawings/figures are intended to be explanatory and not restrictive.

DETAILED DESCRIPTION

Reference will now be made in detail to the various implementations in the present disclosure, examples of which may be illustrated in any accompanying drawings and figures. The implementations are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the implementations.

Throughout the specification and claims, the following terms take the meanings explicitly associated herein, unless the context clearly dictates otherwise. Phrases such as "in an implementation," "in certain implementations," and "in some implementations" as used herein do not necessarily refer to the same implementation(s), though they may. Furthermore, the phrases "in another implementation" and "in some other implementations" as used herein do not necessarily refer to a different implementation, although they may. As described below, various implementations may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes implementations containing A, B, or C, multiple examples of A, B, or C, or combinations of A/B, A/C, B/C, A/B/B/ B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, components, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some implementations, some operations in the procedures, methods, techniques, and workflows disclosed herein may be combined and/or the order of some operations may be changed.

Cetylpyridinium chloride (CPC) is a commonly used cationic antibacterial compound. CPC is soluble in alcohol and in aqueous solutions, and has a neutral pH. CPC acts as an antibacterial by binding and penetrating the negatively-charged surface of bacterial cell membranes to kill bacteria. However, the effectiveness of CPC as an antibacterial agent is reduced or inhibited in the presence of anionic surfactants, such as SLS. While not intending to be bound by any particular theory, it is believed that, when added to aqueous solutions, anionic surfactants ionize and have a negative charge. Accordingly, the negatively-charged anionic surfactant may bind to positively-charged cationic antibacterial molecules, such as CPC, and degrade their antibacterial activity. In other cases, anionic surfactants may cause cationic species to precipitate and thereby deactivate. Similarly, it is believe that the cationic functional groups are also deactivated within strongly alkaline environments, such as those of bar soaps incorporating anionic soaps and surfactants.

However, the inventors have unexpectedly and surprisingly created a new cationic antibacterial agent that is effective in personal care compositions including anionic surfactants and soaps. In particular, the inventors have created a cetylpyridinium complex which maintains effective antibacterial activity in the presence of anionic surfactants, such as SLS.

In certain implementations, the cetylpyridinium complex is a complex of cetylpyridinium chloride (CPC) and a soluble metal salt. The soluble metal salt may be selected from a zinc salt and a stannous salt. For example, the soluble salt may be one of zinc chloride, zinc sulfate, zinc nitrate, zinc bromide, and zinc citrate. In other implementations, the soluble salt may be stannous chloride. In other examples, other divalent (and monovalent) metals may also be used, such as calcium, copper, silver, zirconium, and aluminum.

In one implementation, the cetylpyridinium complex may be a complex of cetylpyridinium chloride (CPC) with zinc chloride ($ZnCl_2$). In other examples, the cetylpyridinium complex may be a complex of cetylpyridinium chloride (CPC) with stannous chloride ($SnCl_2$). Formula 1 illustrates the chemical structure of CPC and $ZnCl_2$. However, as described above, in other implementations, the cetylpyridinium complex may be a complex of cetylpyridinium bromide with zinc chloride ($ZnCl_2$) or zinc bromide ($ZnBr_2$), or a complex of cetylpyridinium chloride (CPC) with zinc bromide ($ZnBr_2$), or a complex of cetylpyridinium chloride (CPC) with stannous chloride ($SnCl_2$).

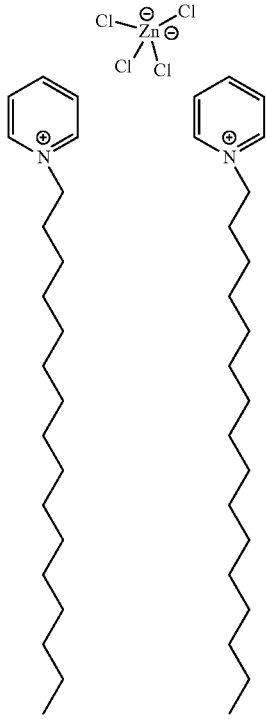

Formula 1

Accordingly, the cetylpyridinium complex may be, for example, a CPC—$ZnCl_2$ complex and/or a CPC—$SnCl_2$ complex, and a personal care composition includes an antibacterial agent, wherein the antibacterial agent comprises the cetylpyridinium complex. In other implementations, the antibacterial agent consists essentially of the cetylpyridinium complex, such as the CPC—$ZnCl_2$ complex. In certain implementations, the personal care composition lacks additional antibacterial agents. For example, the CPC—$ZnCl_2$ complex may be the only antibacterial agent in the personal care composition. In other implementations, the personal care composition may include additional antibacterial agents, such as zinc chloride or other metal salts.

The CPC—$ZnCl_2$ complex may be formed by the combination of CPC and $ZnCl_2$ aqueous solutions. For example, the CPC—$ZnCl_2$ complex may be a solid precipitate formed by the combination of CPC and $ZnCl_2$ aqueous solutions.

In one implementation, the CPC—$ZnCl_2$ complex was produced as follows: a 25 weight % CPC solution was created by dissolving 2.50 grams of anhydrous CPC in 10.01 grams of deionized water and a 75 weight % $ZnCl_2$ solution was created by dissolving 3.66 grams of anhydrous $ZnCl_2$ CPC in 4.90 grams of deionized water. 1.0 grams of the 75 weight % $ZnCl_2$ solution was then added dropwise to 3.76 grams of the 25 weight % CPC solution to obtain a Zn/CPC molar ratio of 2. The 75 weight % $ZnCl_2$ solution immediately precipitated upon contact with the 25 weight % CPC solution to produce the CPC—$ZnCl_2$ complex. In other implementations, the CPC—$ZnCl_2$ complex may be produced with other Zn/CPC molar ratios. For example, the amounts of CPC solution and $ZnCl_2$ solution, or the concentration of the CPC solution and $ZnCl_2$ solution, may be varied to obtain other molar ratios and the CPC—$ZnCl_2$ complex may be produced with a Zn/CPC molar ratio between 0.5 and 2.0. In one implementation, the CPC—$ZnCl_2$ complex may be produced with a Zn/CPC molar ratio of 0.5.

In another implementation, a larger amount of the CPC—$ZnCl_2$ complex was produced as follows: 5.0 grams of the 75% $ZnCl_2$ solution created as above was added dropwise to 18.75 grams of the 25 weight % CPC solution created as above to obtain a solid precipitate. The solid precipitate was then filtered and washed using 500 mL of deionized water followed by 5 mL of methanol and left in a 50° C. oven to dry overnight. The dried powder was chopped into a fine powder in a scintillation vial and left in a 50° C. oven for an hour under vacuum to produce the CPC—$ZnCl_2$ complex.

The CPC—$ZnCl_2$ complex was then mixed with deionized water to create 0.1, 0.5, 1.0, and 10.0 weight % CPC aqueous solutions to evaluated the solubility of the CPC—$ZnCl_2$ complex at both room temperature (23-24° C.) and at physiological temperature (36-37° C.). At room temperature, the 0.1 and 0.5 weight % solutions were soluble, while the 1.0 and 10.0 weight % solutions exhibited undissolved CPC—$ZnCl_2$ complex even after 24 hours of aging. Similarly, at physiological temperature, the 1.0 weight % solution was soluble, whereas the 10 weight % solution was not fully soluble.

In contrast, CPC and $ZnCl_2$ are readily soluble in water. For example, $ZnCl_2$ was readily soluble in water at concentrations of up to 75 weight % at room temperature. Similarly, CPC was readily soluble in water at concentrations of up to 25 weight %, while producing a translucent gel or soft-solid material at concentrations greater than 40 weight % at room temperature.

Accordingly, in some implementations, the CPC—ZnCl$_2$ complex had at least a 25-fold reduction in solubility when compared to the CPC and ZnCl$_2$ reactants separately.

Similarly, CPC has a melting point of 77° C. In contrast, in some implementations, the CPC—ZnCl$_2$ complex transforms into a gel form at around 50° C. The reduction in solubility and changes in melting point are evidence that the CPC—ZnCl$_2$ complex is not a mere mixture of CPC and ZnCl$_2$, but involves a covalently or ionically-bound complex.

FIG. 1 illustrates the full spectrum (FTIR-ATR) infrared spectroscopy of samples of CPC—ZnCl$_2$ complex and CPC according to an implementation.

Figure 2:
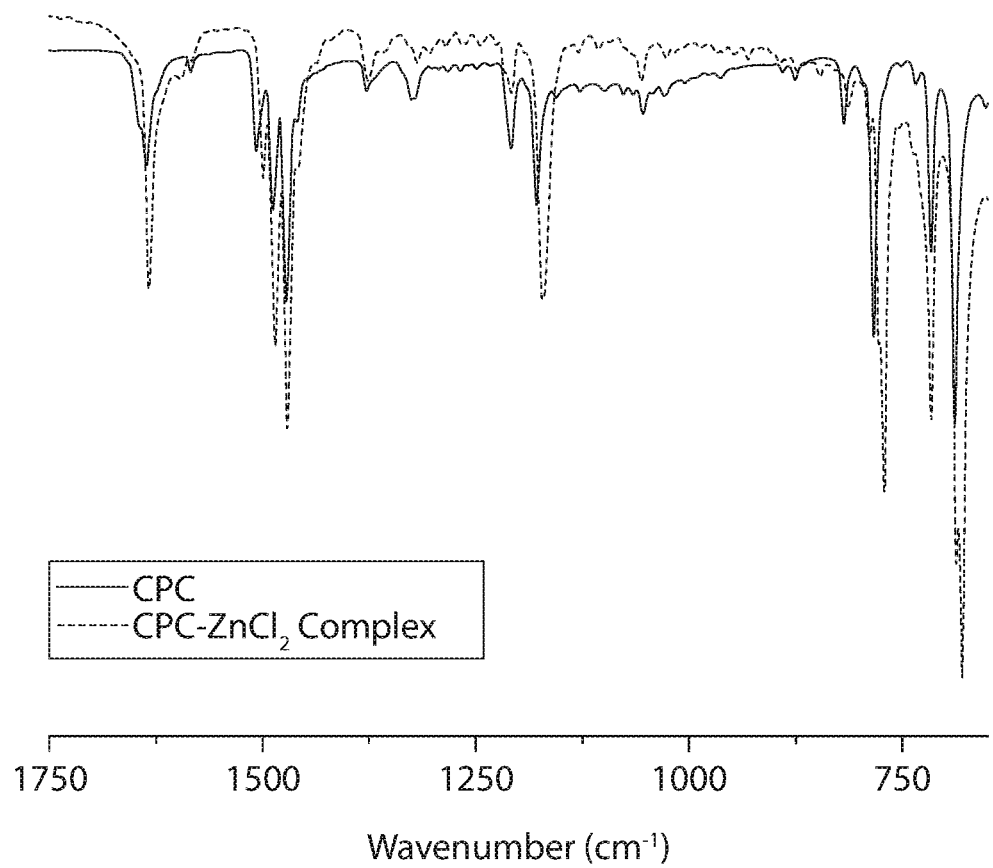
FIG. 2 illustrates the fingerprint region (FTIR-ATR) infrared spectroscopy of the CPC—$ZnCl_2$ complex and CPC samples of FIG. 1.

FIG. 2 illustrates the fingerprint region (FTIR-ATR) infrared spectroscopy of the CPC—ZnCl$_2$ complex and CPC samples of FIG. 1.

As illustrated in FIGS. 1 and 2, the most notable difference between the infrared spectroscopy for the CPC—ZnCl$_2$ complex and CPC is observed at the medium strength absorption band located around 3300 cm$^{-1}$, where after the addition of the ZnCl$_2$ and thermal treatment the CPC's band at 3300 cm$^{-1}$ splits into two (possible symmetric and asymmetric counterparts) distinct bands. That is, FIG. 1 illustrates significant changes in the Nitrogen vibrations (ca. 3500 cm$^{-1}$). This is more apparent in the fingerprint region illustrated in FIG. 2. The fingerprint region of FIG. 2 shows significant shifts/changes throughout the whole region which suggests structural differences of the CPC—ZnCl$_2$ complex and CPC samples further evidencing that the CPC—ZnCl$_2$ complex is not a mere mixture of CPC and ZnCl$_2$, but involves a covalently or ionically-bound complex.

A CPC—ZnCl$_2$ complex sample for elemental analysis was created by mixing 0.046 g of the CPC—ZnCl$_2$ complex as created above with 9.20 g of deionized water. The elemental analysis indicated 0.11 weight % Zn and 0.15 weight % Cl present in the solution. Accordingly, the elemental analysis suggests a Cl$^-$/Zn$^{2+}$ molar ratio of 2.5 which corresponds to the stoichiometry of 2 ZnCl$_2$:1 CPC, and is consistent with 2 ZnCl$_2$ molecules chelating a single Cl$^-$ from the CPC structure generating a [Zn$_2$Cl$_5$] moiety.

Accordingly, in certain implementations, the CPC—ZnCl$_2$ complex is a solid precipitate. The CPC—ZnCl$_2$ complex may also have a significantly reduced water solubility when compared to CPC.

To further elucidate the differences between the CPC—ZnCl$_2$ complex and CPC, samples of the CPC—ZnCl$_2$ complex prepared as described above were dissolved in solvent and re-crystallized to study implementations of its crystalline structure. In particular, crystals of the CPC—ZnCl$_2$ complex were made suitable for X-ray crystallography by dissolving samples of the CPC—ZnCl$_2$ complex (prepared as described above) in acetone and methanol, and re-crystallizing the CPC—ZnCl$_2$ complex by slow evaporation at room temperature. The X-ray diffraction data was collected using a Bruker D8 Venture PHOTON 100 CMOS system equipped with a Cu Kα INCOATEC ImuS microfocus source ($\lambda$=1.54178 Å). The X-ray diffraction data was collected at both 100 K and 298 K for the CPC—ZnCl$_2$ complex dissolved in methanol (Sample A) and at both 100 K and 273 K for the CPC—ZnCl$_2$ complex dissolved in acetone (Sample B). Indexing was performed using APEX3 (Difference Vectors method). Data integration and reduction were performed using SaintPlus 6.01. Absorption correction was performed by multi-scan method implemented in SADABS. Space group was determined using XPREP implemented in APEX3. The crystalline structure of the CPC—ZnCl$_2$ complex was solved using SHELXT (direct methods) and was refined using SHELXL-2017 (full-matrix least-squares on F$^2$) through OLEX2 interface program. All non-hydrogen atoms were refined anisotropically. Hydrogen atoms were placed in geometrically calculated positions and were included in the refinement process using riding model.

Figure 3:
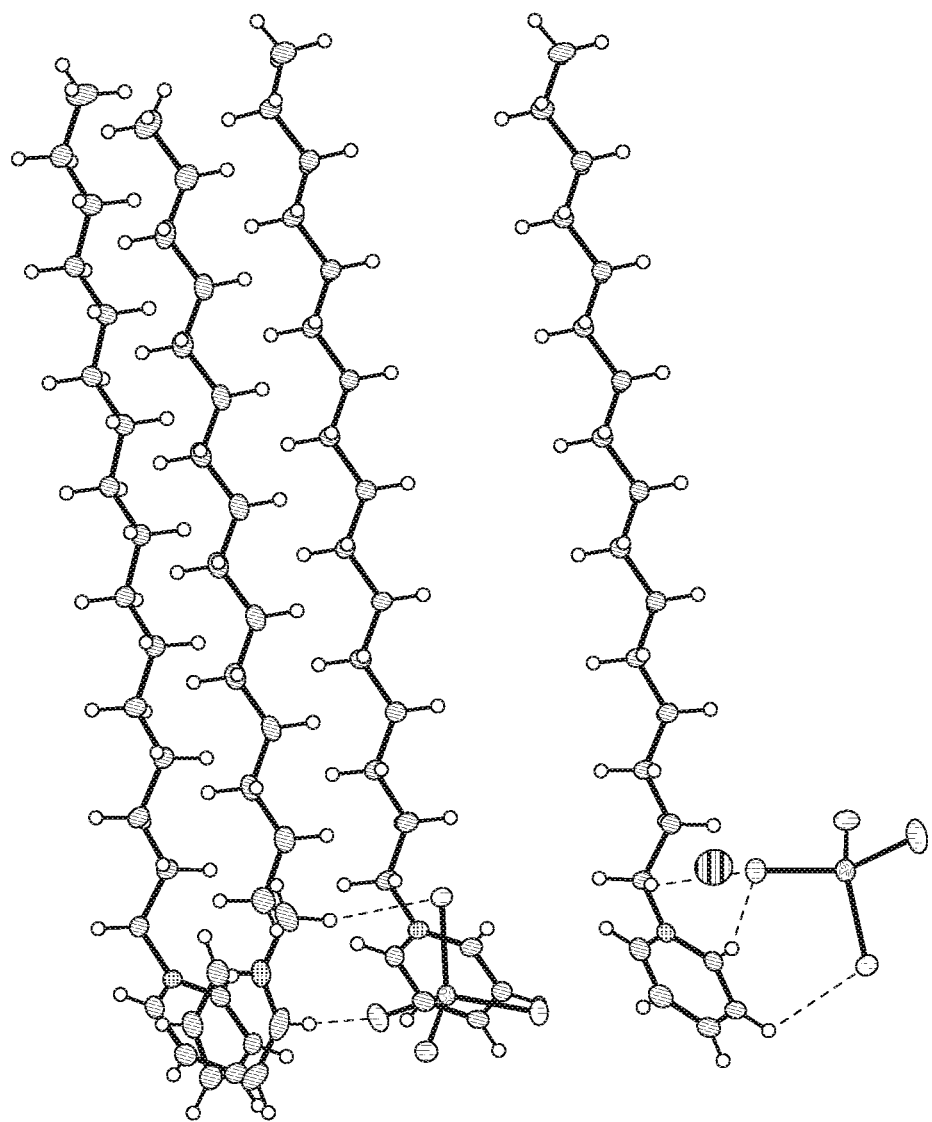
FIGS. 3-4 illustrate an X-ray diffraction (SCXRD) analysis of a CPC—$ZnCl_2$ complex according to an implementation.
Figure 4:
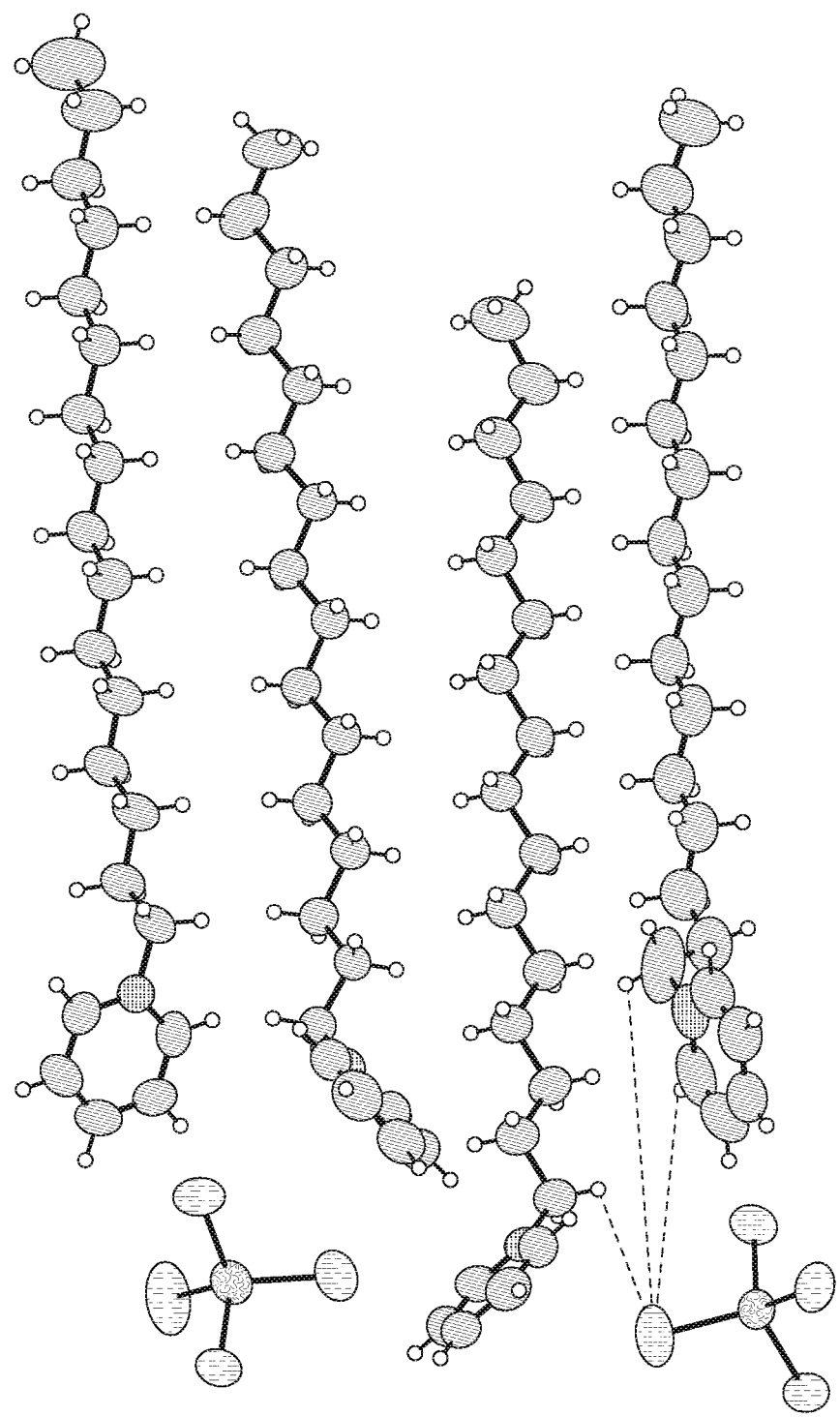

FIGS. 3-4 illustrate an X-ray diffraction (SCXRD) analysis of a CPC—ZnCl$_2$ complex according to an implementation. In particular, these figures illustrates a single crystal X-ray diffraction (SCXRD) analysis of Sample B at both 100 K(FIG. 3) and at 298 K (FIG. 4). As illustrated in FIGS. 3-4, the single crystal X-ray diffraction (SCXRD) analysis carried out both at 100 K and 298 K shows that the coordination complex crystallizes in orthorhombic Pbca space group. At 100 K (FIG. 3), the structural formula of the CPC—ZnCl$_2$ complex may be described as [(C$_{21}$H$_{38}$N)$_2$][ZnCl$_4$].O, where four independent cationic CPC units are present along with two anionic ZnCl$_4^{2-}$ units. The tetrahedral ZnCl$_4^{2-}$ anions are slightly distorted with the largest Cl—Zn—Cl angle being 113.40°. The average Zn—Cl bond distance is 2.27 Å which is in the range of the distances reported for the isolated ZnCl$_4^{2-}$ anions (2.26-2.29 Å) in the Cambridge Structural Database (CSD). The bond distances and angles for the organic cations also match quite well with those reported in the literature. The pyridinium heads are present close to the anions while the alkyl chains point in the opposite direction for the cation. Three of the CPC units have an eclipsed conformation while the other unit stacks slightly above the plane containing the three units. The as-synthesized crystals contain disordered solvent that was modeled as water molecule (atom O1). The unit cell parameters for Sample B were calculated as (a=14.08, b=20.51, c=62.56).

Figure 5:
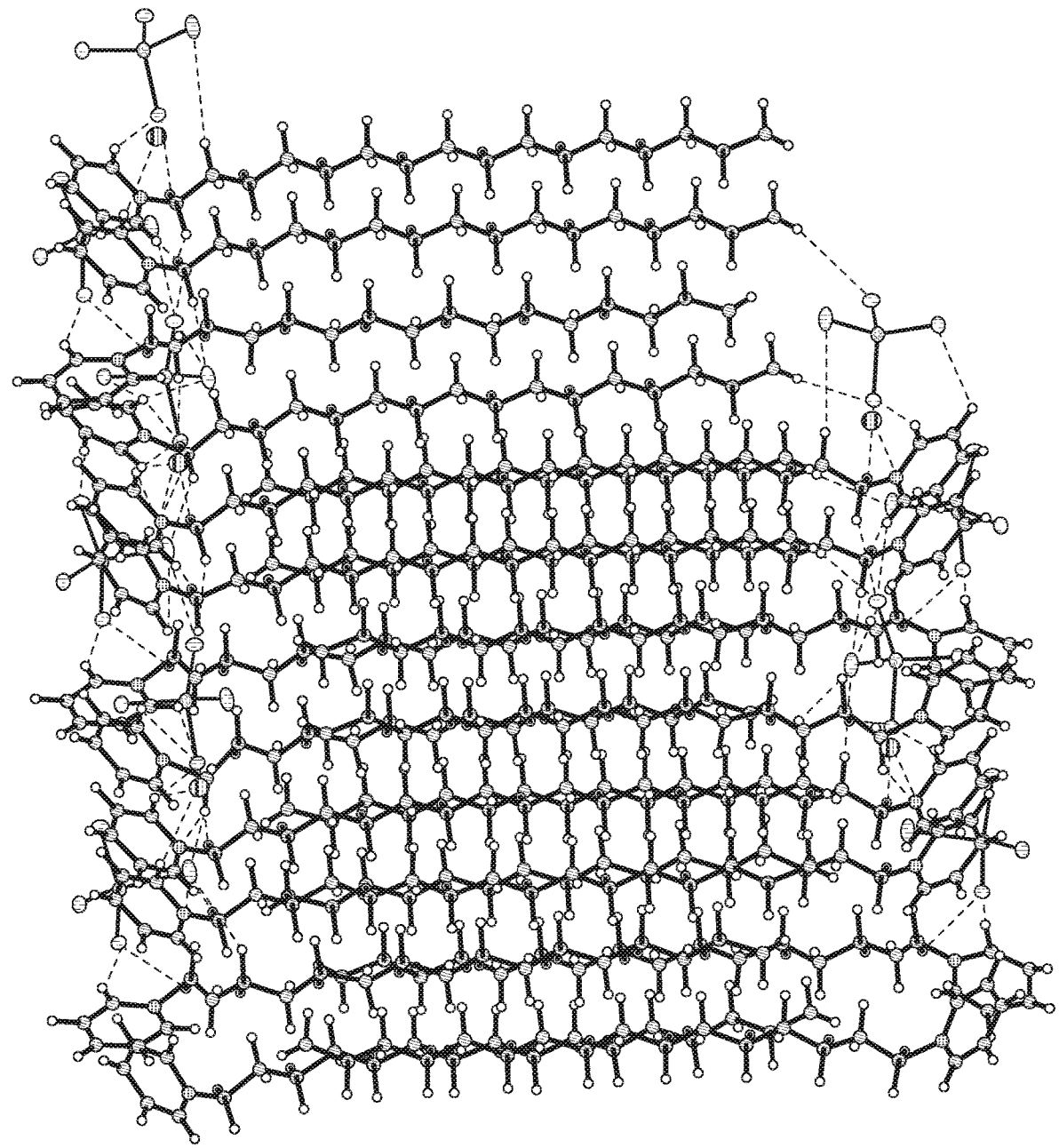
FIG. 5 illustrates packing of the structure illustrated in FIG. 3.

FIG. 5 illustrates packing of the structure illustrated in FIG. 3. As illustrated in FIG. 5, in some implementations, the packing arrangement of the CPC—ZnCl$_2$ complex analyzed at 100 K is similar to other reported [C16-Py]$_2$[MX$_4$] salts (M=Pd, Cd; X=Cl, Br) having a typical layer structure with alternating polar and apolar regions. A high degree of interdigitation is present within the apolar region.

The ionic layer is generated via repetition of superimposed rows of the pyridinium rings along the a axis. There are two different types of superimposed rows followed by superimposed rows of cations, which are again followed by two different superimposed rows of the pyridinium rings and different superimposed rows of cations. These are held together by C—H—Cl type secondary H-bonding interactions present between the chlorine atoms of the anion and the H atoms of the pyridinium ring and the alkyl chain (alpha and gamma H-atoms). The solvent oxygen atom also shows a weak interaction with the H-atom of the pyridinium ring. The H—Cl distances are in the range of the H-bonds with intermediate to weak strength and the number of C—H—Cl-M type interactions per ion pair and the distances are comparable to analogous Pd and Cd structures. The superimposed rows of pyridinium rings are interdigitated by the other superimposed rows of the next pyridinium ring and no significant π-π interactions are observed.

Figure 6:
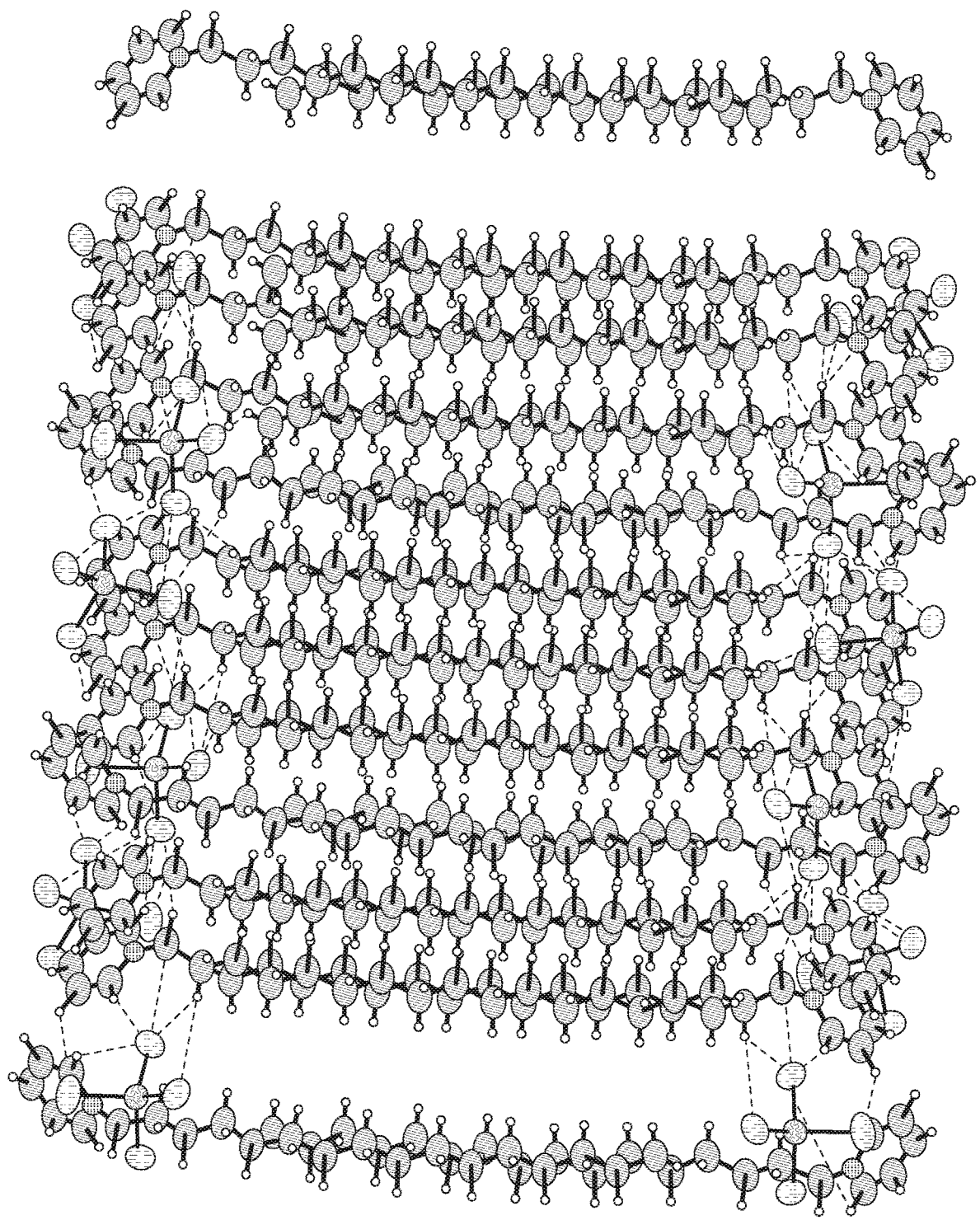
FIG. 6 illustrates packing of the structure illustrated in FIG. 4.

FIG. 6 illustrates packing of the structure illustrated in FIG. 4. As illustrated in FIG. 6, in some implementations, upon increasing the temperature to 298 K, the arrangement of the cationic and the anionic units relative to each other changes and the unit cell parameters change with the "a" unit cell parameter increasing significantly from 14.08 Å to 14.67 Å. At 298 K, the solvent molecule gets removed and the structural formula for the CPC—ZnCl$_2$ complex may be described as [(C$_{21}$H$_{38}$N)$_2$][ZnCl$_4$]. As illustrated in FIGS. 4 and 6, two of the CPC units are in an eclipsed conformation and the $ZnCl_4^{2-}$ anions are present between these units and another CPC unit. Another CPC unit lies underneath the eclipsed CPC units (FIG. 4).

As illustrated in FIG. 6, the packing behavior at 298 K is similar to the packing behavior at 100 K (FIG. 5), with layers being generated from the repetition of superimposed rows of the pyridinium rings along the a axis and the pairs of two types of superimposed rows of anions followed by superimposed rows of cations held together by the secondary C—H—Cl type hydrogen bonding interactions. The range of the H—Cl distances falls in the H-bonds with intermediate to weak strength and there are no significant π-π interactions present. The distance between the zinc (II) centers (Zn01-Zn2) increases from 8.73 Å (at 100 K) to 9.05 Å (at 298 K).

Figure 7:
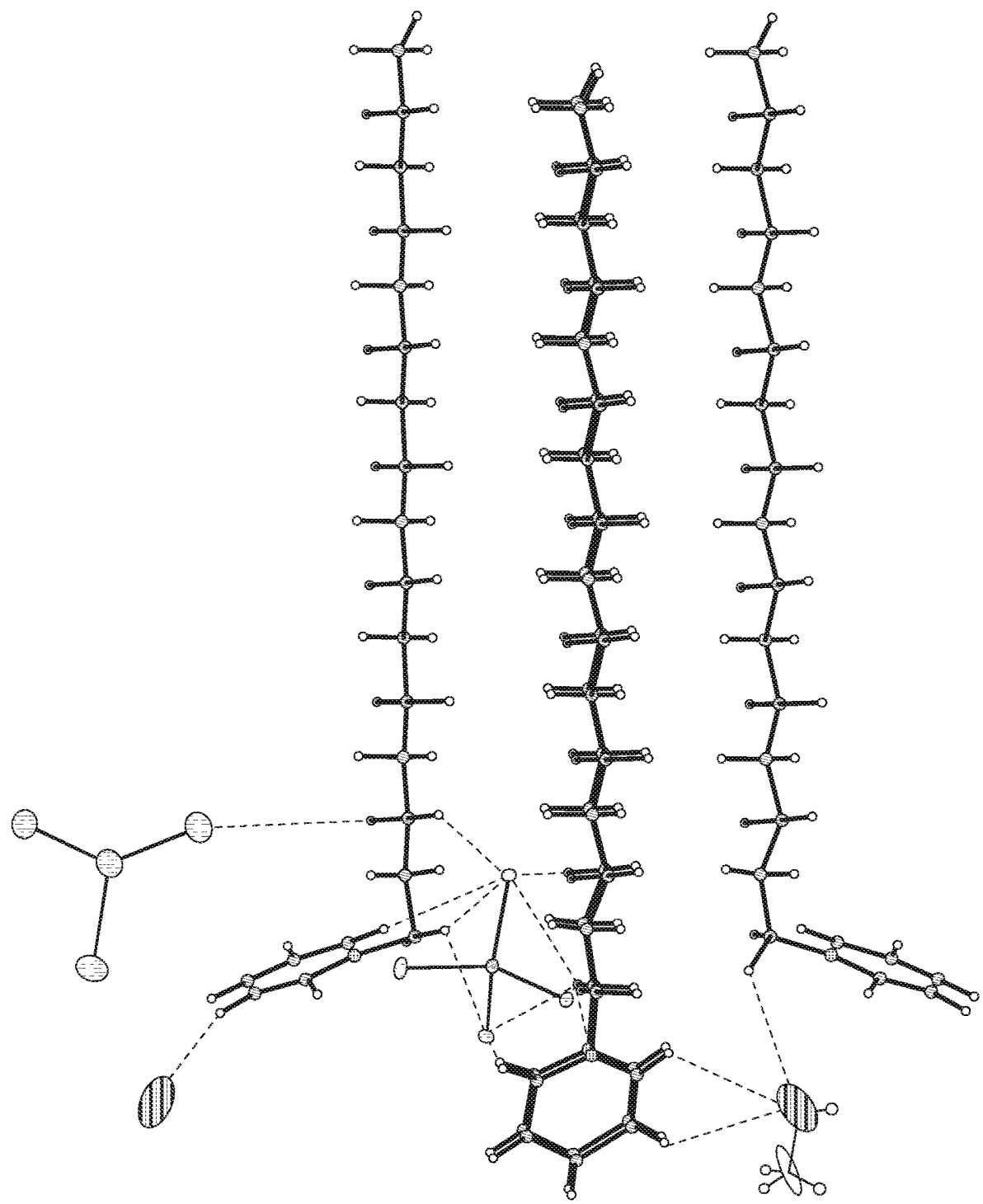
FIGS. 7-8 illustrate an X-ray diffraction (SCXRD) analysis of a CPC—$ZnCl_2$ complex according to an implementation.
Figure 8:
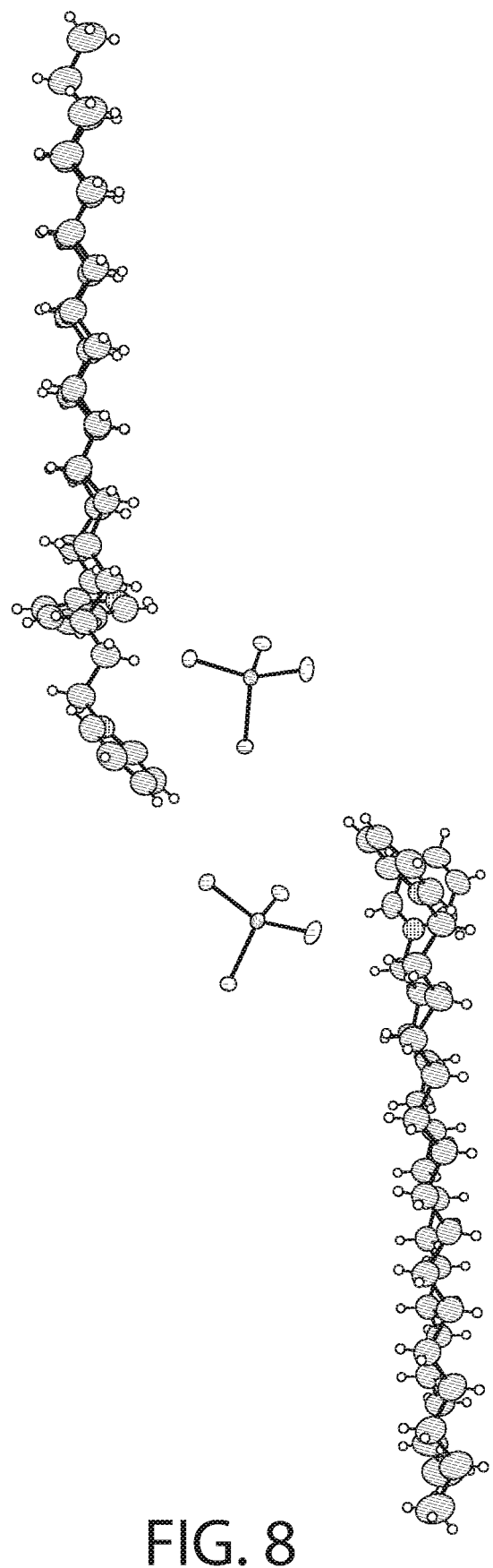

FIGS. 7-8 illustrates an X-ray diffraction (SCXRD) analysis of a CPC—$ZnCl_2$ complex according to an implementation. In particular, these figures illustrates a single crystal X-ray diffraction (SCXRD) analysis of Sample A at both 100 K (FIG. 7) and at 273 K (FIG. 8). As illustrated in FIGS. 7-8, the re-crystallization from methanol gave rise to a CPC—$ZnCl_2$ complex that may be described as $[(C_{21}H_{38}N)_2][ZnCl_4].O.(CH_3OH)$. In certain implementations, this structure has the similar four independent cationic CPC units and the two anionic $ZnCl_4^{2-}$ units, but may display a different unit cell and packing of the structure. For example, the SCXRD analysis carried out at both 100 K (FIG. 7) and 273 K (FIG. 8) revealed that Sample A crystallizes in the monoclinic P2(1)/c space group. The unit cell parameters (a=33.26, b=9.06, c=32.05) for Sample A at 100 K may be different from Sample B (a=14.08, b=20.51, c=62.56). As illustrated in FIGS. 7-8, there may be an elongation along the a axis and a decrease along the b and the c axis. In the asymmetric unit, two of the CPC units are eclipsed onto each other with one anionic $ZnCl_4^{2-}$ unit present between the two eclipsed CPC units and another CPC unit. Another CPC unit is stacked above the eclipsed CPC units. The structure contains disordered solvent which was modeled as water molecule (atom O1). Another solvent molecule is present that was modeled as methanol. The structural formula can be described as $[(C_{21}H_{38}N)_2][ZnCl_4].O.(CH_3OH)$.

As illustrated in FIGS. 7-8, the tetrahedral $ZnCl_4^{2-}$ anions are slightly distorted. One of the anionic unit has a significant distortion with the Cl—Zn—Cl angle being 119.50° due to disorder in the Cl atom. The average Zn—Cl bond distance (2.27 Å) lies in the 2.26-2.29 Å range of the distances reported for the isolated $ZnCl_4^{2-}$ anions in the Cambridge Structural Database (CSD).

Figure 9:
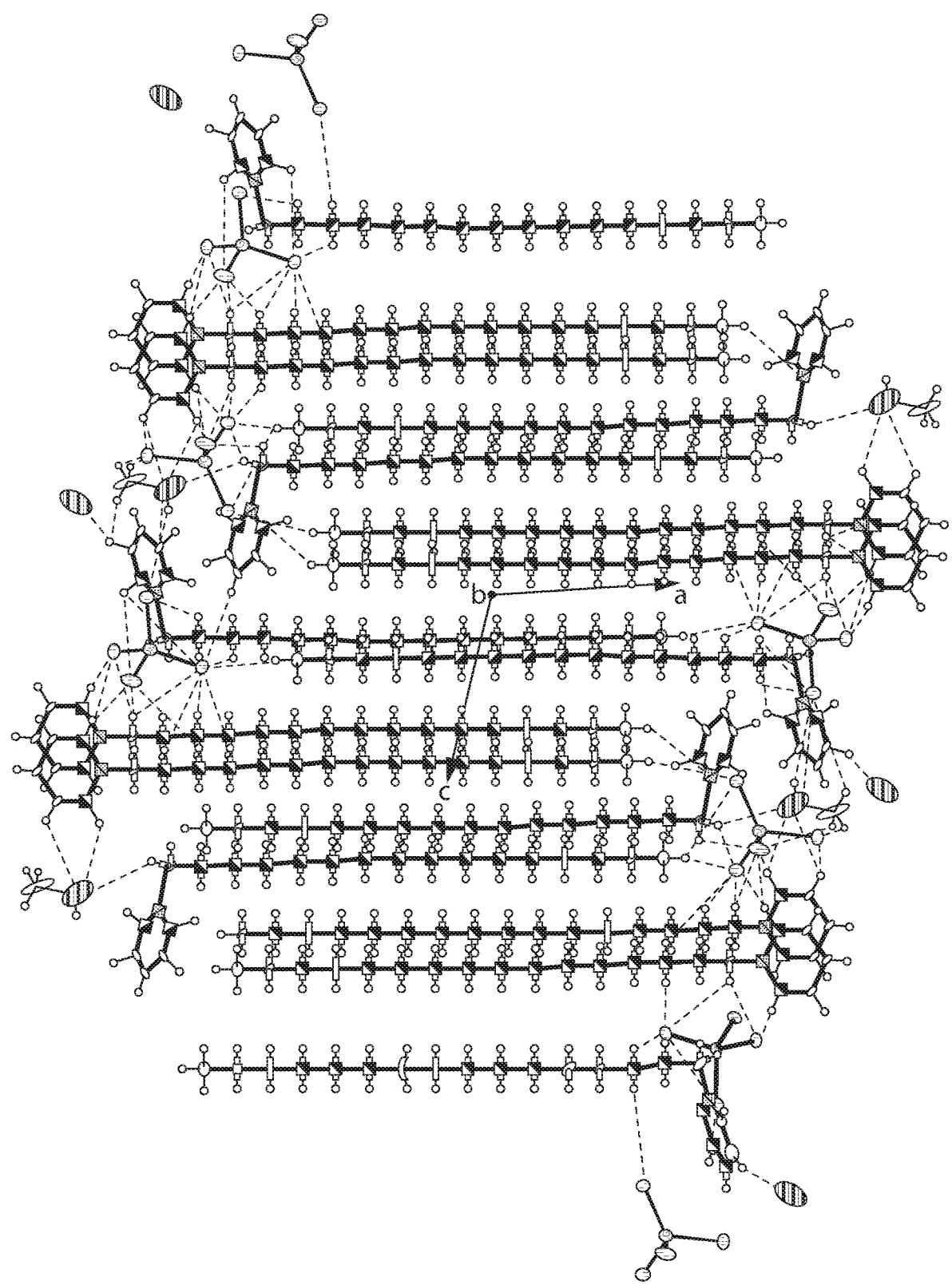
FIG. 9 illustrates packing of the structure illustrated in FIG. 7.

FIG. 9 illustrates packing of the structure illustrated in FIG. 7. As illustrated in FIG. 9, in some implementations, the packing arrangement of the CPC—$ZnCl_2$ complex analyzed at 100 K is similar to that of Sample B (layer structure with alternating polar and apolar regions) illustrated in FIG. 5. There is a high degree of interdigitation and the layer is generated via repetition of superimposed rows of the pyridinium rings along the b axis. There are two different types of superimposed rows of cations followed by the two different superimposed rows of anions. The supramolecular arrangement is attained via the secondary hydrogen bonding interactions of the C—H—Cl type and between the solvent oxygen and pyridinium hydrogen atoms. No significant π-π interactions are present.

Figure 10:
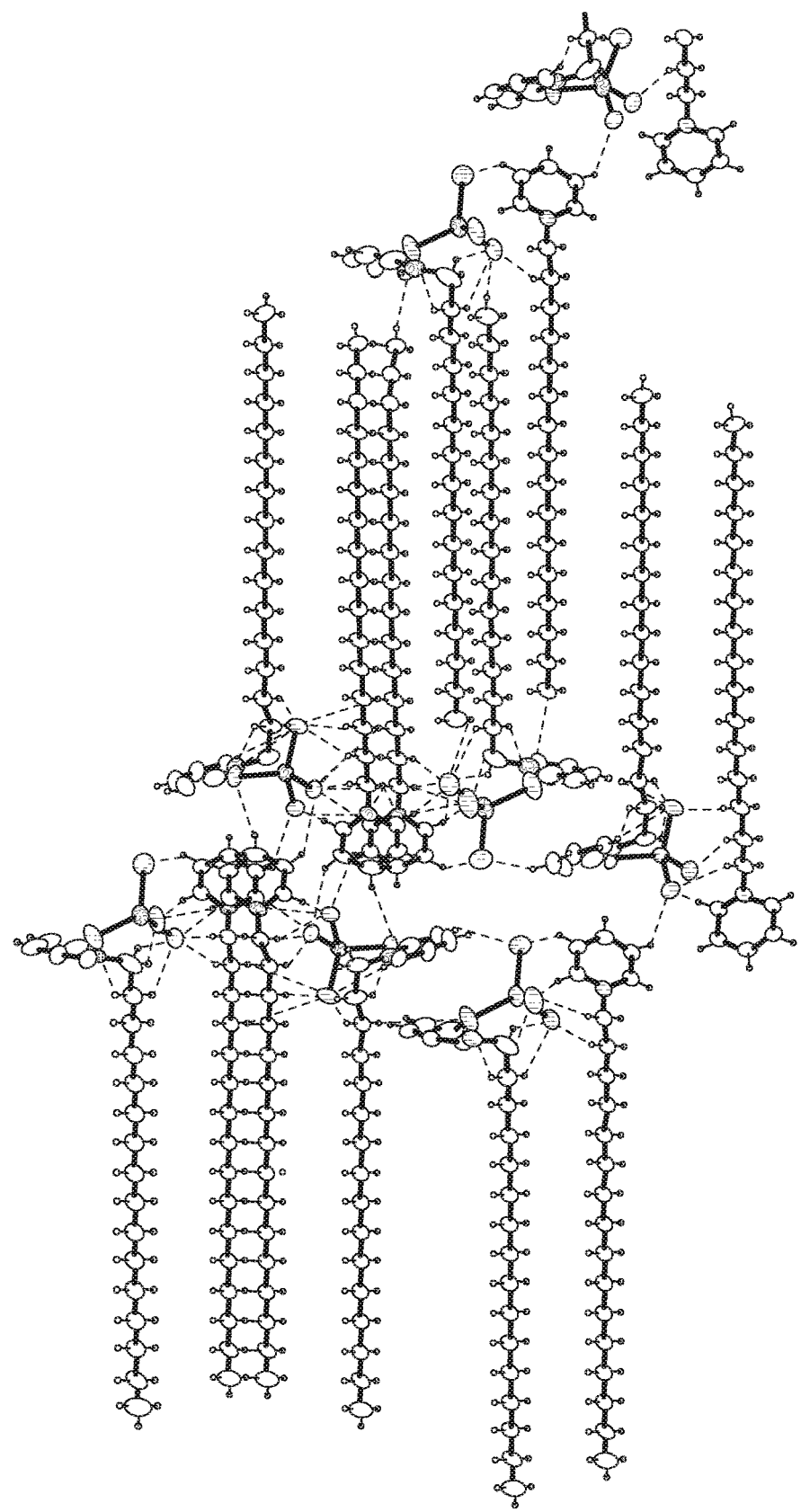
FIG. 10 illustrates packing of the structure illustrated in FIG. 8.

FIG. 10 illustrates packing of the structure illustrated in FIG. 8. As illustrated in FIG. 10, in some implementations, upon increasing the temperature to 273 K, structure adopts a different conformation with the two $ZnCl_4^{2-}$ anions present between the two pairs of two eclipsed CPC units. The unit cell parameters are also different from the 100 K structure with the c parameter increasing significantly from 32.05 Å to 32.98 Å. The distance between the zinc (II) centers (Zn01-Zn02) decreases from 8.94 Å (at 100 K) to 8.71 Å (at 273 K). The packing is similar having the layer structure with alternating polar and apolar regions with a high degree of interdigitation. The secondary hydrogen bonding interactions of the C—H—Cl type are stronger compared to the above structures but no significant π-π interaction is there.

Figure 11:
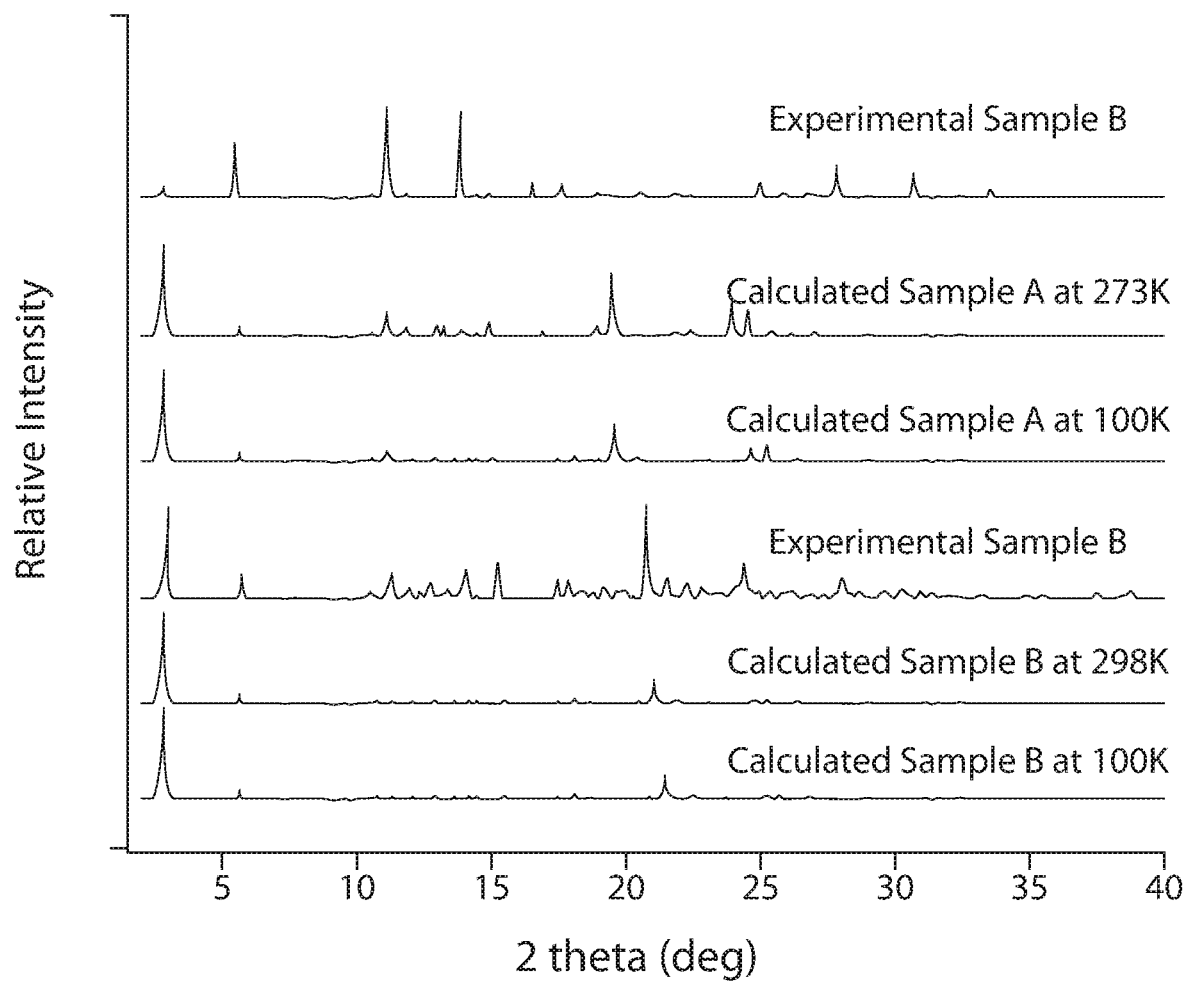
FIG. 11 illustrates a powder X-ray diffraction (PXRD) analysis of CPC—$ZnCl_2$ complex samples according to various implementations.

FIG. 11 illustrates a powder X-ray diffraction (PXRD) analysis of CPC—$ZnCl_2$ complex samples according to implementations. As illustrated in FIG. 11, powder X-ray diffraction (PXRD) analysis of the re-crystallized CPC—$ZnCl_2$ complex samples (Samples A and B) showed that it is in good agreement with the calculated structures at both 100 K and 298 K, confirming phase purity.

Accordingly, as illustrated in FIGS. 3-11, in some implementations, the CPC—$ZnCl_2$ complex can be described as having a $[(C_{21}H_{38}N)_2][ZnCl_4]$ structural formula. In addition, the crystallization analysis described above further evidence that the CPC—$ZnCl_2$ complex is not a mere mixture of CPC and $ZnCl_2$, but involves a covalently or ionically-bound complex.

In other implementations, the cetylpyridinium complex may be a complex of cetylpyridinium chloride (CPC) with a stannous chloride ($SnCl_2$).

The CPC—$SnCl_2$ complex may be formed by the combination of CPC and $SnCl_2$ aqueous solutions. For example, the CPC—$SnCl_2$ complex may be a solid precipitate formed by the combination of CPC and $ZnCl_2$ aqueous solutions. In one implementations, the CPC—$SnCl_2$ complex was formed as follows: a 10 weight % and a 25 weight % solutions was prepared using stannous chloride dihydrate ($SnCl_2.2H_2O$) and cetylpyridinium chloride monohydrate ($CPC.H_2O$), respectively, in absolute ethanol. The solutions were then sonicated to ensure complete dissolution. The stannous chloride solution was then added dropwise to the CPC solution. A crystalline "snow-flake" type material was then formed after several minutes. This material was filtered, washed with copious amounts of water, and characterized via ATR-FTIR and SCXRD to illustrate its nature as a CPC—$SnCl_2$ complex.

Figure 12:
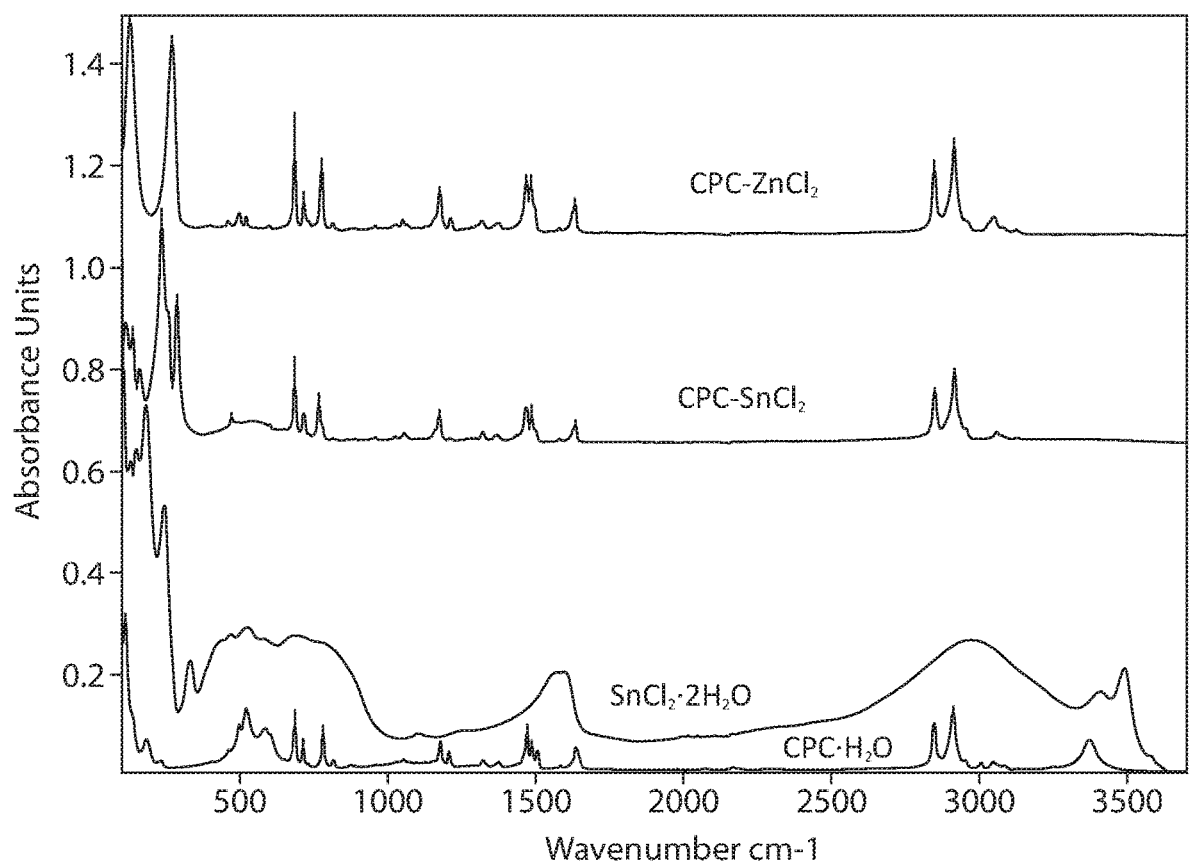
FIG. 12 illustrates a full spectrum (FTIR-ATR) infrared spectroscopy for samples of CPC—$ZnCl_2$ complex, CPC—$SnCl_2$ complex, $SnCl_2 \cdot 2H_2O$, and $CPC \cdot H_2O$ according to an implementation.
Figure 13:
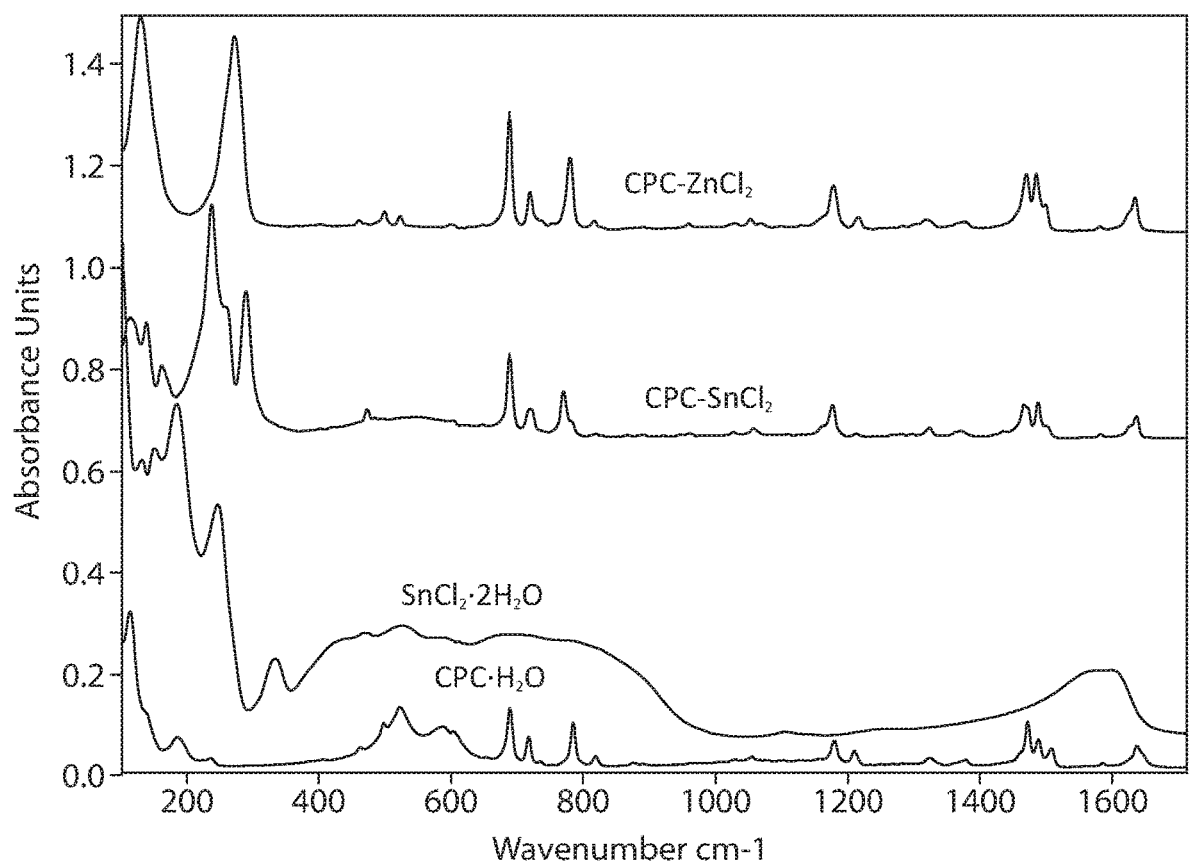
FIG. 13 illustrates a close-up view of the FTIR-ATR infrared spectroscopy of FIG. 12 in the 100-1700 cm-1 range.

FIG. 12 illustrates the full spectrum (FTIR-ATR) infrared spectroscopy of samples of CPC—$ZnCl_2$ complex, CPC—$SnCl_2$ complex, $SnCl_2.2H_2O$, and $CPC·mH_2O$ according to an implementation. FIG. 13 illustrates a close-up view of the FTIR-ATR infrared spectroscopy of FIG. 12 in the 100-1700 cm-1 range. The Infrared spectra was collected using a Bruker Vertex 70 FTIR spectrometer (Bruker Optics, Billerica, Mass.) equipped with a GladiATR diamond ATR accessory (Pike technologies, Madison, Wis.). The spectral range was 80-4000 $cm^{-1}$ and a resolution of 4 $cm^{-1}$ was used. All measurements were carried out at room temperature.

As illustrated in FIGS. 12-13, the spectrum of the CPC—$SnCl_2$ complex sample clearly shows the fingerprint of the cetylpyridinium, confirming its presence in the sample. However, a close inspection of the spectrum also demonstrates that the bands of cetylpyridinium in the CPC—$SnCl_2$ complex sample do not match the pure $CPC.H_2O$ starting material: a majority of the bands related to $CH_2$, C=C, C=N and C—H stretching and bending vibrations of cetylpyridinium display shifted peak positions compared to the $CPC·H_2O$ starting material. The ν(OH) band near 3370 $cm^{-1}$ seen in $CPC.H_2O$ starting material has also disappeared in presence of Sn. Furthermore, a new cluster of bands below 340 $cm^{-1}$ (e.g., strong bands at 289, 260 and 237 $cm^{-1}$) is evident in the CPC—$SnCl_2$ complex sample, likely originating from the Sn-related vibrations. Comparison to the $SnCl_2 \cdot 2H_2O$ starting material spectrum does not reveal presence of residual $SnCl_2.2H_2O$ starting material in the CPC—$SnCl_2$ complex sample. In addition, it is noteworthy that the spectra of the CPC—$SnCl_2$ complex sample and the CPC—$ZnCl_2$ complex sample are overall similar in the behavior of the cetylpyridinium vibrational bands in presence of metal. Accordingly, the FTIR data of FIGS. 12-13 evidence that the CPC—$SnCl_2$ complex is not merely a mixture of CPC and $SnCl_2$, but the formation of a new cetylpyridinium complex.

Figure 14:
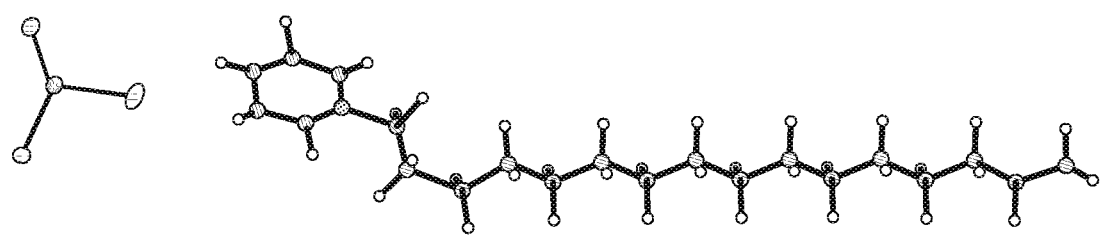
FIG. 14 illustrates an X-ray diffraction (SCXRD) analysis of a CPC—$SnCl_2$ complex according to an implementation.
Figure 15:
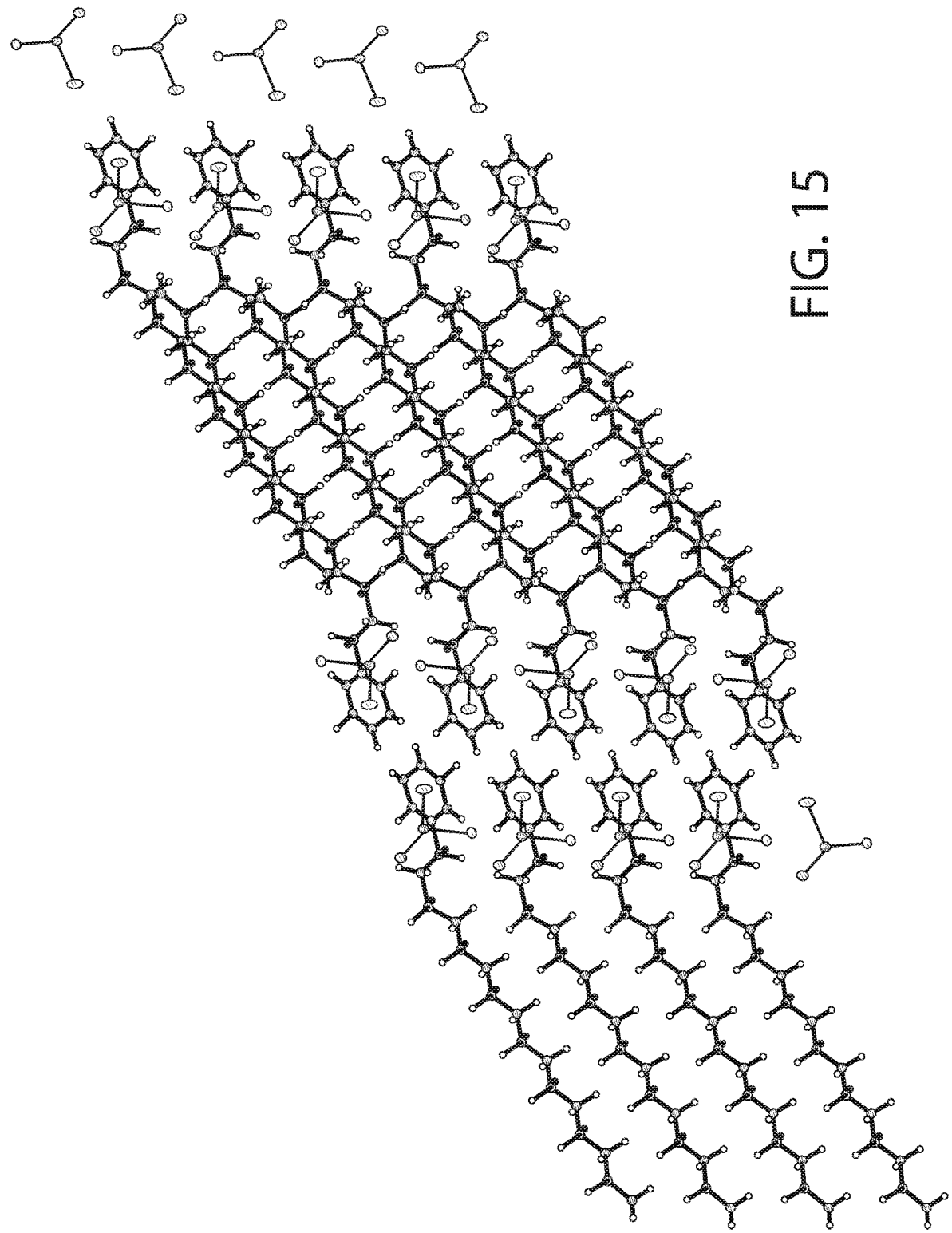
FIG. 15 illustrates packing of the structure illustrated in FIG. 14.

FIG. 14 illustrates an X-ray diffraction (SCXRD) analysis of a CPC—$SnCl_2$ complex according to an implementation. FIG. 15 illustrates packing of the structure illustrated in FIG. 14. The X-ray diffraction data was collected using a Bruker D8 Venture PHOTON 100 CMOS system equipped with a Cu K$\alpha$ INCOATEC ImuS micro-focus source ($\lambda$=1.54178 Å). Data integration and reduction were performed using SaintPlus 6.01. Absorption correction was performed by multi-scan method implemented in SADABS. Space group was determined using XPREP implemented in APEX3. The structure was solved using SHELXT (direct methods) and was refined using SHELXL-2017 (full-matrix least-squares on F2) through OLEX2 interface program. All non-hydrogen atoms were refined anisotropically. Hydrogen atoms were placed in geometrically calculated positions and were included in the refinement process using riding model.

As illustrated in FIGS. 14-15, the solved crystal structure and packing arrangement for the CPC—$SnCl_2$ complex show that the molecules are arranged in a 1:1 ratio with a cetylpyridinium cation and $SnCl_3$ anion. The alkyl chains of CPC align with one another with the polar head groups facing in opposite directions for consecutive molecules. The pyridine rings are aligned in parallel in respect to one another. As a result of the packing arrangement (FIG. 15), there is a non-polar region consisting of the stacked alkyl chains and a polar region consisting of the cationic pyridine rings and $SnCl_3^-$ anions.

Accordingly, as illustrated in FIGS. 12-15, in some implementations, the CPC—$SnCl_2$ complex can be described as having a $[C_2H_{38}N][SnCl_3]$ structural formula. In addition, the crystallization analysis described above further evidence that the CPC—$SnCl_2$ complex is also not a mere mixture of CPC and $SnCl_2$, but involves a covalently or ionically-bound complex.

In some implementations, the cetylpyridinium complex, such as the CPC—$ZnCl_2$ complex, has increased antibacterial activity when compared to CPC or $ZnCl_2$ in the presence of anionic surfactants, such as SLS.

In addition, the cetylpyridinium complex, such as the CPC—$ZnCl_2$ complex, may have significantly reduced water solubility when compared to CPC or $ZnCl_2$ while still exhibiting antibacterial activity. In some implementations, due to its reduced solubility, a personal care composition incorporating the cetylpyridinium complex, such as the CPC—$ZnCl_2$ complex, is more stable in all pH ranges as the CPC—$ZnCl_2$ complex remains a solid and has limited interaction with the environment of the personal care composition.

As described in the present disclosure, the inventors have created a novel antibacterial agent including a cetylpyridinium complex, such as the CPC—$ZnCl_2$ complex and/or the CPC—$SnCl_2$ complex, that can be incorporated into personal care compositions incorporating anionic soaps and surfactants. In some implementations, the CPC—$ZnCl_2$ complex has a structural formula of $[(C_{21}H_{38}N)_2][ZnCl_4]$ and the CPC—$SnCl_2$ complex has a structural formula of $[C_{21}H_{38}N][SnC_3]$. The personal care composition may include both rinse-off compositions and leave-on compositions. Rinse-off compositions include but are not limited to bar soap, body wash, shower gel, shampoo, conditioner, liquid hand or other soap, dish soap and facial wash; and leave-on compositions include lotions, including but not limited to hand lotion and body lotion, creams including but not limited to facial cream, diaper cream and sunscreen cream, and underarm products including but not limited to deodorant and/or antiperspirant sticks, gels, roll-on and pump sprays.

In some implementations, the cetylpyridinium complex, such as the CPC—$ZnCl_2$ complex, is the only antibacterial agent in the personal care composition. In other implementations, the cetylpyridinium complex is part of a mixture of antibacterial agents in the personal care composition.

The personal care composition may include an amount of cetylpyridinium complex sufficient to inhibit or retard the growth of bacteria on skin or hair. In one implementation, the personal care composition may include from about 0.01 weight % to about 8 weight % CPC—$ZnCl_2$ complex, based on the total weight of the personal care composition. For example, the personal care composition may include from about 0.01 weight % to about 5 weight % CPC—$ZnCl_2$ complex, from about 0.01 weight % to about 2 weight % CPC—$ZnCl_2$ complex, from about 0.05 weight % to about 1.0 weight % CPC—$ZnCl_2$ complex, from about 0.10 weight % to about 0.75 weight % CPC—$ZnCl_2$ complex, or from about 0.25 weight % to about 0.50 weight % CPC—$ZnCl_2$ complex, based on the total weight of the personal care composition. In other implementations, the personal care composition may include from about 0.01 weight % to about 8.0 weight % CPC—$SnCl_2$ complex, based on the total weight of the personal care composition.

In a preferred implementation, the personal care composition is a bar soap and includes from about 0.01 weight % to about 8.0 weight % cetylpyridinium complex, such as the CPC—$ZnCl_2$ complex.

In other implementations, the personal care composition a liquid personal care composition and includes about 0.25 weight % or less cetylpyridinium complex, such as the CPC—$ZnCl_2$ complex, based on the total weight of the personal care composition. For example, the personal care composition may include from about 0.001 weight % to about 0.20 weight % CPC—$ZnCl_2$ complex, from about 0.001 weight % to about 0.15 weight % CPC—$ZnCl_2$ complex, from about 0.001 weight % to about 0.10 weight % CPC—$ZnCl_2$ complex, from about 0.01 weight % to about 0.10 weight % CPC—$ZnCl_2$ complex, or from about 0.05 weight % to about 0.10 weight % CPC—$ZnCl_2$ complex. In other implementations, the personal care composition may include from about 0.001 weight % to about 0.20 weight % CPC—$SnCl_2$ complex, based on the total weight of the personal care composition.

The personal care composition may be manufactured according to conventional methods known to those skilled in the art. For example, the personal care composition may be prepared by adding the cetylpyridinium complex in a particular weight ratio, and combining it in a carrier that also includes other ingredients that are suitable for use in a personal care product.

Unless otherwise specifically identified, additional ingredients for use in the personal care compositions of the present disclosure are preferably cosmetically acceptable ingredients. As used herein, "cosmetically acceptable" means suitable for use in a formulation for topical application to human skin or hair. A cosmetically acceptable excipient, for example, is an excipient which is suitable for external application in the amounts and concentrations contemplated in the formulations, and includes, for example, excipient which are "Generally Recognized as Safe" (GRAS) by the United States Food and Drug Administration. In addition, the additional ingredients should not substantially inhibit the efficacy of the antibacterial agent described herein.

The personal care composition may include a carrier. For example, the personal care composition may include carriers that are well known in the art. The carrier may be a liquid, semi-solid or solid. Carriers among those useful herein include liquids, pastes, ointments, and gels, and can be transparent, translucent or opaque. The carrier may comprise any of a variety of materials, including emulsifiers, thickeners, fillers, and preservatives. In certain implementations, the carrier is specifically selected to ensure that there is no substantially reduction in efficacy for the antibacterial agent(s). For example, the personal care composition may use water as the carrier. In certain implementations, the personal care composition includes 90 weight % or less, 70 weight % or less, or 50 weight % or less carrier, based on the total weight of the personal care composition.

The personal care composition may also include one or more surfactants. In some implementations, the surfactants enhance stability of the composition, help clean skin surfaces through detergency, and provide foam upon agitation. In various implementations, suitable surfactants may function as a surface active agent, emulsifier, and/or foam modulator.

Any cosmetically acceptable surfactant, most of which are anionic, nonionic, cationic, or amphoteric, may be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

The personal care composition may include one or more additional antibacterial agents or preservatives. In some implementations, the preservatives improve an antimicrobial characteristic of the personal care composition to improve storage life or prevent decay.

In certain implementations, the one or more antibacterial agents or preservatives are included in the personal care composition, preferably at a concentration of about 0.01 weight % to about 10 weight %, about 0.01 weight % to 3 weight %, or 0.01 weight % to 2.5 weight %, based on the total weight of the personal care composition. Examples of preservatives include, but are not limited to, EDTA, benzalkonium chloride; sodium salicylate; benzethonium chloride, 5-bromo-5-nitro-1,3dioxane; 2-bromo-2-nitropropane-1,3-diol; alkyl trimethyl ammonium bromide; N-(hydroxymethyl)-N-(1,3-dihydroxymethyl-2,5-dioxo-4-imidaxolidinyl-N-(hydroxyl methyl)urea; 1-3-dimethyol-5,5-dimethyl hydantoin; formaldehyde; iodopropynil butyl carbamate, butyl paraben; ethyl paraben; methyl paraben; propyl paraben, mixture of methyl isothiazolinone/methylchloroisothiazoline in a 1:3 weight ratio; mixture of phenoxyethanol/butyl paraben/methyl paraben/propylparaben; 2-phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadamantane chloride; sodium benzoate, sodium salicylate; organic acids, lactic acid, or citric acid, triclosan, and combinations thereof.

In some implementations, the personal care composition includes an antioxidant. Acceptable antioxidants include BHA, BHT, vitamin A, vitamin C, carotenoids, vitamin E, flavonoids, polyphenols, ascorbic acid, herbal antioxidants, chlorophyll, melatonin and mixtures thereof. The personal care composition may include 0.01 weight % or more antioxidants.

The personal care composition may include an emollient. Illustrative examples of such emollient include glycerine, glyceryl oleate, caprylyl glycol, triglycerides (e.g., caprylic/capric triglyceride), silicone oils (e.g., cyclomethicone), ester oils (e.g., butyl myristate, isopropyl myristate, cetyl myristate, isopropyl palmitate, isopropyl stearate, octyl stearate, isocearyl stearate), organic fatty alcohols (e.g., oleic alcohol, linolenic alcohol, linoleic alcohol, isostearyl alcohol, octyl dodecanol).

In certain implementations, the personal care composition may include one or more humectants. In some implementations, the humectant is a mixture of humectants, such as glycerin and sorbitol, and a polyhydric alcohol, such as propylene glycol, butylene glycol, hexylene glycol, polyethylene glycol.

In some implementations, the personal care composition may also include one or more pH modifying agents. The pH modifying agents among those useful herein include acidifying agents to lower pH, basifying agents to raise pH and buffering agents to control pH within a desired range. For example, one or more compounds selected from acidifying, basifying, and buffering agents may be included to provide a pH of 2 to 10, or in various illustrative implementations 2 to 8, 3 to 9, 4 to 8, 5 to 7, 6 to 10, 7 to 9, etc. In preferred implementations, the pH is between about 1 to 5, about 2 to 5, about 4 to 5, or about 4.2-4.8. Examples of pH modifying agent include HCl, phosphoric and sulfonic acids and carboxylic acids, such as lactic acid and citric acid, acid salts (e.g., monosodium citrate, disodium citrate, monosodium malate, etc.), alkali metal hydroxides, such as sodium hydroxide and potassium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an acceptable pH range. Preferably, only one pH modifying agent is employed.

The personal care composition may also include a rheology modifier useful, for example, to inhibit settling or separation of ingredients or to promote an acceptable usage experience. In some implementations, the rheology modifier is selected from an inorganic salt, isopropyl palmitate, isopropyl myristate, a polymer, salts or other electrolytes, such as e.g., sodium chloride, and other mono-, di- and trivalent salts, and a hydrotrope. In some implementations, the rheology modifier includes a brine solution comprising sodium chloride. One or more rheology modifiers are optionally present in a total amount of 0.01 weight % to 10 weight %, for example 0.1 weight % to 8 weight %, or about 0.01 weight % to about 6 weight % based on the total weight of the personal care composition.

In some implementations, the personal care composition may include one or more optional ingredients selected from coloring agents, fragrances, moisturizing agents, amino acids, and pearlizers.

The personal care composition may further include skin care ingredients, such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self-tanning, soothing, as well as agents to improve elasticity and skin barrier and/or further UV-filter substances and carriers and/or excipients or diluents conventionally used in topical personal care compositions.

The personal care composition may also contain usual cosmetic or cleaning adjuvants and additives, such as water-soluble alcohols; glycols; glycerides; medium to long chain organic acids, alcohols and esters; additional amino acids; structurants; fatty substances and/or oils; organic solvents, silicones; thickeners; softeners; emulsifiers; active sunscreen agents; moisturizers; aesthetic components, such as fragrances; fillers; sequestering agents; anionic, cationic, nonionic or amphoteric polymers; propellants; acidifying or basifying agents; dyes; colorings/colorants; abrasives; absorbents; essential oils; skin sensates; astringents; pigments or nanopigments; e.g. those suited for providing a photoprotective effect by physically blocking out ultraviolet radiation; plants, herbs or parts or extracts thereof, e.g., seaweed; or any other ingredients usually formulated into cosmetic or cleaning personal care compositions. Such ingredients commonly used in the skin care industry, which are suitable for use in the personal care compositions of the present disclosure may be described in the CTFA Cosmetic Ingredient Handbook, Second Edition (1992) without being limited thereto. In some implementations, the necessary amounts of the cosmetic and dermatological adjuvants and additives may be based on the desired product or type of personal care composition and may be easily be chosen by a skilled person in the art.

EXAMPLES

Aspects of the present disclosure may be further understood by referring to the following examples. The examples are illustrative, and are not intended to be limiting implementations thereof.

Example 1

Table 1 illustrates an evaluation of the antibacterial efficacy of a CPC—$ZnCl_2$ complex in the presence of an anionic surfactant. In particular, the antibacterial efficacy of a CPC—$ZnCl_2$ complex was compared to $ZnCl_2$ and CPC individually, in the presence of SLS, as follows: human saliva was collected and diluted three times with deionized water, centrifuged, and decanted to yield a translucent solution of oral bacteria. 10 mg (+/−0.7 mg) of the antibacterial ingredient (CPC—$ZnCl_2$ complex, CPC, and $ZnCl_2$) was combined with 20 mg (+/−0.9 mg) of a 30 weight % SLS aqueous solution and 5 ml of the prepared oral bacteria solution. A negative control was also prepared adding 20 mg (+/−0.9 mg) of the 30 weight % SLS aqueous solution and 5 ml of the prepared oral bacteria solution to deionized water instead of the antibacterial ingredient. The samples were then placed in a 37° C. oven and shaken at 100 RPM for 30 minutes. 200 µL of Alamar Blue dye was then added to each sample and placed back in the 37° C. oven and shaken at 100 RPM. The samples were then monitored every 30 minutes, with the results 1 hour after addition of the dye recorded in Table 1. Under an Alamar Blue assay, a color change from blue to red indicates the presence of live bacteria.

TABLE 1

| Active | Color of Solution |
| --- | --- |
| CPC-$ZnCl_2$ complex | Blue |
| CPC | Pink |
| $ZnCl_2$ | Purple |
| Control | Pink |

As illustrated in Table 1, both the Control and the CPC sample turned pink, indicating the presence of live bacteria. The $ZnCl_2$ sample turned purple, also indicating the presence of live bacteria. However, the CPC—$ZnCl_2$ complex sample remained blue, indicating the absence of live bacteria. The results of Table 1 demonstrate that cationic antibacterial-metal salt complexes of the present invention provide antimicrobial efficacy, even in the presence of an anionic surfactant. These results are truly surprising given the anticipated interaction between cationic antibacterial agents and anionic surfactants, which renders cationic antibacterial agents largely ineffective. As such, these results provide a breakthrough in formulating cationic antibacterial agents with anionic surfactants. The data described Table 1 also illustrates that the CPC—$ZnCl_2$ complex is not a mere mixture of CPC and $ZnCl_2$; rather, it is a distinct chemical entity. Without being bound by theory, the results observed herein suggest the presence of a covalently or ionically-bound complex.

Example 2

Table 2 describes a bar soap composition according to some implementations of the present disclosure. Table 3 describes a roll-on antiperspirant and/or deodorant composition according to some implementations of the present disclosure.

TABLE 2

| Ingredients | Wt. % |
| --- | --- |
| CPC-$ZnCl_2$ | 0.1-5.0% |
| Sodium Soap Chips | 78-99% |
| Colorants | 0-1.0% |
| $TiO_2$ | 0-1.0% |
| Fragrance | 0-0.15% |
| Free fatty acids | 0-2.0% |

TABLE 3

| Ingredients | Wt. % |
| --- | --- |
| CPC-$ZnCl_2$ complex | 0.1-5.0% |
| Glycerin | 5.0-10% |
| Steareth-2 | 1.0-2.0% |
| Bees wax | 0.5-5.0% |
| Water | 40-60% |
| Preservation | 0.1-1.0% |

TABLE 3-continued

| Ingredients | Wt. % |
| --- | --- |
| Colorants | 0.1-0.5% |
| Stereth-20 | 1.0-5.0% |
| Cetyl alcohol | 0-6.0% |

The exemplary compositions described in Tables 2 and 3 (above) may be prepared according to conventional methods known to those skilled in the art. In particular, the exemplary compositions are prepared to ensure that the CPC—$ZnCl_2$ complex provides effective antibacterial activity in compositions incorporating anionic surfactants (e.g. SLS) or soaps.

Example 3

Separate vials containing twenty-five percent (25%) solutions of CPC and seventy-five percent (75%) solutions of $ZnCl_2$ are prepared. These solutions are then diluted 10×, 100×, and 1000×, and kept in separate vials. Thereafter, each of the diluted CPC and $ZnCl_2$ solutions are combined at a Zn:CPC molar ratio of 2:1 (e.g. the 0X diluted solution of CPC is combined with the 10× diluted solution of $ZnCl_2$). A precipitate was only observed at concentrations significantly higher than those likely to be used in personal care compositions. These results demonstrate that the complexes of the present invention do not spontaneously form in compositions comprising typical concentrations of CPC and $ZnCl_2$. While the examples above describe a molar ratio, the present disclosure is not limited thereto, and other molar ratios may be used to create the complexes of the present disclosure. For example, the CPC and $ZnCl_2$ solutions may be combined at other molar ratios to create the CPC—$ZnCl_2$ complex. In one implementation, the Zn:CPC molar ratio may be 0.5-2.0:1. In another implementation, the Zn:CPC molar ratio may be 0.1-4.0:1.

The present disclosure has been described with reference to exemplary implementations. Although a few implementations have been shown and described, it will be appreciated by those skilled in the art that changes may be made in these implementations without departing from the principles and spirit of preceding detailed description. It is intended that the present disclosure be construed as including all such modifications and alterations insofar as they come within the scope of the appended claims or the equivalents thereof.

What is claimed is:

1. A personal care composition, comprising:
    a complex comprising a cationic antibacterial agent comprising cetylpyridinium chloride (CPC) and a metal salt comprising zinc chloride, wherein the complex has a structural formula of $[(C_{21}H_{38}N)_2][ZnCl_4]$;
    a surfactant; and
    a cosmetically acceptable carrier;
    wherein the personal care composition is in a form selected from: a bar soap, a liquid hand soap, a shower gel, a body wash, a shampoo, a facial cleanser, a cream, an antiperspirant, and a deodorant.

2. The personal care composition according to claim 1, wherein the surfactant is an anionic surfactant selected from: sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylate, sodium dodecyl benzenesulfonate; and combinations of two or more thereof.

3. The personal care composition according to claim 1, comprising from about 0.01 weight % to about 8.0 weight % of said complex.

4. The personal care composition according to claim 1, comprising from about 0.10 weight % to about 0.75 weight % of said complex.

5. The personal care composition according to claim 1, wherein the personal care composition is in the form of a bar soap.

6. The personal care composition according to claim 1, wherein the personal care composition is in a form selected from an antiperspirant and a deodorant.

7. The personal care composition according to claim 1, further comprising one or more ingredients selected from a fragrance; a skin conditioning agent, a moisturizing agent, a dye, a pigment, a chelating agent, a sunscreen active ingredient, an antiaging compound, an antioxidant, a vitamin, an essential oil, and a combination of two or more thereof.

* * * * *